United States Patent [19]

Failla

[11] Patent Number: 4,579,118
[45] Date of Patent: Apr. 1, 1986

[54] HEMOSTATIC CLIP WITH PENETRATION MEANS

[75] Inventor: Stephen J. Failla, Chester, N.J.

[73] Assignee: Ethicon, Inc., Somerville, N.J.

[21] Appl. No.: 500,062

[22] Filed: Jun. 1, 1983

[51] Int. Cl.⁴ ............................................. A61B 17/12
[52] U.S. Cl. ..................................... 128/325; 128/305
[58] Field of Search ............... 128/325, 326, 346, 337, 128/305

[56] References Cited

U.S. PATENT DOCUMENTS

| | | | |
|---|---|---|---|
| 3,150,666 | 9/1964 | Auerbach | 128/326 |
| 3,378,010 | 4/1968 | Codling et al. | 128/325 |
| 3,463,156 | 8/1969 | McDermott | 128/325 |
| 3,584,628 | 6/1971 | Green | 128/326 |
| 3,856,016 | 12/1974 | Davis | 128/325 |
| 4,112,951 | 9/1978 | Hulka et al. | 128/325 |
| 4,394,864 | 7/1983 | Sandhaus | 128/325 |
| 4,434,795 | 3/1984 | Mericle | 128/325 |
| 4,449,531 | 5/1984 | Cerwin et al. | 128/325 |
| 4,450,839 | 5/1984 | Transue | 128/325 |

Primary Examiner—C. Fred Rosenbaum
Assistant Examiner—Gene B. Kartchner
Attorney, Agent, or Firm—Robert L. Minier

[57] ABSTRACT

The clip has a latch disposed at the distal end of the leg members to hold the clip in a closed position. The distal end of one of the leg members includes a sharp pointed member directed towards the other of said leg members to penetrate tissue adjacent the vessel to be closed when the clip is closed.

2 Claims, 10 Drawing Figures

HEMOSTATIC CLIP WITH PENETRATION MEANS

The present invention relates to hemostatic clips and more particularly to hemostatic clips fabricated from absorbable and non-absorbable polymeric materials.

BACKGROUND OF THE INVENTION

In many surgical procedures it is often necessary to ligate a plurality of vessels in the surgical site. The vessels may then be severed down-stream of the ligated portion. In some instances the vessel may be ligated at spaced apart areas and the portion of the vessel between the ligations removed. The primary reason for ligating the vessels is to maintain the surgical site free from an excess of blood and to reduce blood loss in the patient. Also, in certain surgical procedures wherein tumors or parts of organs and the like are to be removed, the tumor or organ may have to be separated from certain vessels, and before separating the vessels will have to be ligated.

In the past, the closing of the vessel was usually accomplished using ligatures; that is, threads or filaments which the surgeon ties around the vessel desired to be closed, a very time consuming process and one in which positive closure of the vessel is not always accomplished. In relatively recent years hemostatic clips have replaced the ligatures in many surgical procedures to close blood vessels and other small fluid ducts. These hemostatic clips have been narrow U-shaped or V-shaped strips made from tantalum or stainless steel which are capable of being deformed and possess sufficient strength to retain the deformation when clamped about a blood vessel.

Representative hemostatic clips of the prior art are best illustrated in U.S. Pat. Nos. 3,867,944, 3,631,707, 3,439,523, 3,439,522, 3,666,628, 3,312.216, and 3,270,745.

Very recently the hemostatic clips made from absorbable or non-absorbable polymeric materials have been developed and are being used in various surgical procedures. These polymeric hemostatic clips are more fully described and disclosed in copending patent applications Ser. No. 282,461 filed July 13, 1981, now U.S. Pat. No. 4,418,694, and Ser. No. 276,131 filed June 22, 1981, now abandoned.

The polymeric clips described generally comprise a pair of leg members attached in some manner at their proximal ends. Very often this attachment is in the form of a resilient hinge portion although other means of attachment may be used. The leg members contain smooth innersurfaces disposed towards one another and called the vessel clamping surfaces. It is these surfaces which contact the vessel and close the vessel when the clip is closed. The distal ends of the leg member terminate in an interlocking latch means. The latch means must extend beyond the vessel to be clamped and clear the vessel in order to lock.

Unlike the metal clips which may be deformed about a vessel, the polymeric hemostatic clip as described above latches over the vessel and, hence, surrounds the entire vessel. This means that to use such clips made from the absorbable or non-absorbable polymeric materials, the vessel to be ligated must be free or fully dissected from the surrounding tissue so that the clip may entirely encircle the periphery of the vessel. In many surgical procedures there are a number of small vessels and for the surgeon to have to fully dissect these vessels is a very time consuming process. With the metal clip the surgeon does not have to dissect these vessels but can place the clip on the vessel and about surrounding tissue and deform the clip so that it closes the vessel. This is not true with the clips made from polymeric materials.

An object of the present invention is to produce a clip from absorbable and non-absorbable polymeric materials which may be used to close vessels which have not been fully dissected from the surrounding tissue.

Another object of the present invention is to reduce the time required in a surgical procedure to place hemostatic clips made from polymeric materials.

It is yet another object of the present invention to produce a hemostatic clip from polymeric materials wherein the clip has a latch means that can part the tissue and engage and lock the clip about the vessel although there is tissue adjacent the vessel to be closed.

These and other objects of the present invention will be more fully understood from the following description and drawings.

SUMMARY OF THE PRESENT INVENTION

The present invention provides an improvement in a hemostatic clip made from absorbable or non-absorbable polymeric materials. The clips comprise a pair of leg members attached at their proximal ends. In the preferred embodiments of the clips of the present invention the leg members are attached at their proximal ends in a resilient hinge portion. The leg members include vessel clamping innersurfaces disposed towards one another. The distal ends of the leg members terminate in interlocking latch means. In a preferred embodiment of the clip of the present invention the latch means comprises a deflectable hook portion at the distal end of one leg member which encloses the distal end of the opposite leg member when the clip is closed. The outside surface of the leg members includes means for holding and manipulating the clip using an appropriate clip applying instrument. The improvement of the present invention comprises means cooperating with the latch means to penetrate tissue adjacent the vessel to be closed. This penetrating means aids in insuring a tissue free latch which interlocks when the leg members are closed about a vessel even if the vessel has not been fully dissected from surrounding tissue. In certain embodiments, the improvement may comprise a pointed member extending from the deflectable hook portion with the pointed member disposed so as to penetrate tissue immediately ahead of the deflectable hook portion. In other embodiments of the clips of the present invention wherein the latch means comprises a protrusion extending from one vessel clamping surface towards the opposite vessel clamping surface which protrusion interlocks with a suitable opening in the opposite vessel clamping surface, the protrusion itself may be configured by sharpening and pointing to act as the tissue penetrating means.

BRIEF DESCRIPTION OF THE DRAWINGS

The invention will be more fully described in conjunction with the accompanying drawings wherein.

DETAILED DESCRIPTION OF THE INVENTION

Figure 1:
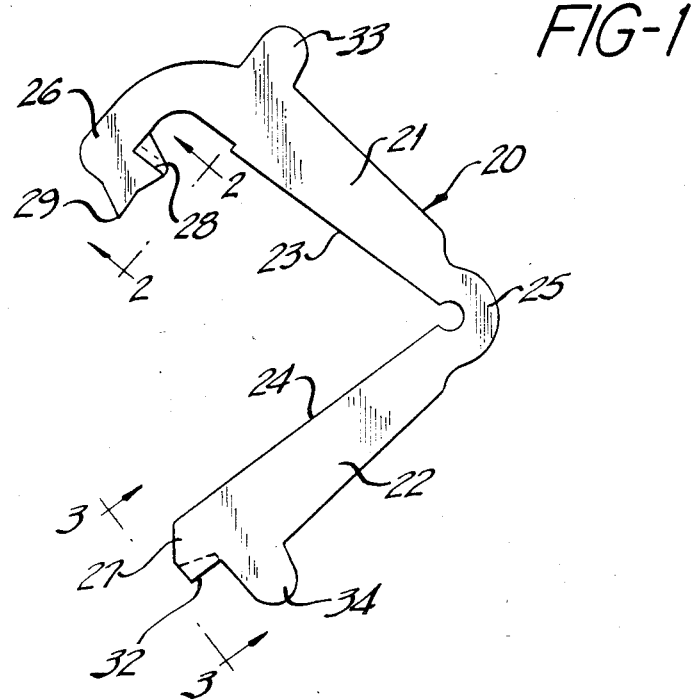
FIG. 1 is a perspective view of an improved hemostatic clip of the present invention.
Figure 2:
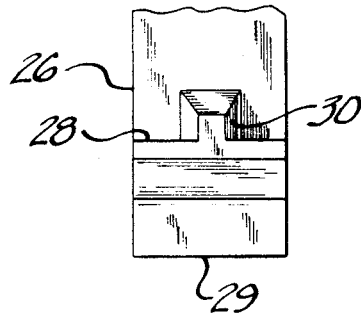
FIG. 2 is a front view taken along line 2—2 of FIG. 1.
Figure 3:
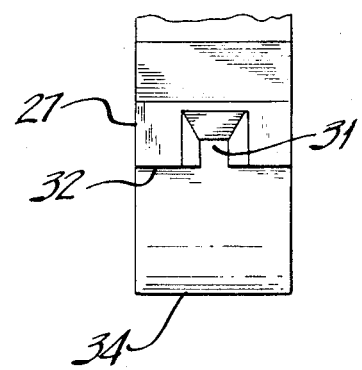
FIG. 3 is a front view taken along line 3—3 of FIG. 1.

Referring to the drawings, there is shown an improved clip 20 of the present invention. As depicted in FIG. 1, the clip comprises a pair of leg members 21 and 22 having opposed vessel clamping surfaces 23 and 24. The leg members are connected at their proximal ends by a resilient hinge portion 25. The distal end of one of the leg members terminates in a return bend hook portion 26. The opposite leg member is somewhat shorter and terminates at its distal end in a portion 27 which can be grasped by the hook portion. The end of this leg member is angled at an obtuse angle to the vessel clamping surface. This angle aids in deflecting the hook portion as the two leg members are brought together about the hinge and allows the hook portion to deflect and then accept the leg member in the area between the innersurface 28 of the hook portion and the vessel clamping surface 23 of the opposite leg member. The hook portion includes a sharpened pointed end 29 extending from the hook portion and positioned to lead the hook portion or preceed the hook portion as the clip is being closed. As shown in FIG. 2, the hook portion has a protrusion 30 dispersed from the central portion of its inner surface 28. This protrusion fits into the recess 31 positioned in the outer surface 32 of the opposite leg member 22. The protrusion and recess interlock when the clip is closed to prevent lateral movement of the leg members. The outside surfaces of the leg members each include a cylindrical boss 33 and 34 for use in holding the clip in a suitable instrument and applying the clip from said instrument as will hereinafter be described.

Figure 4:
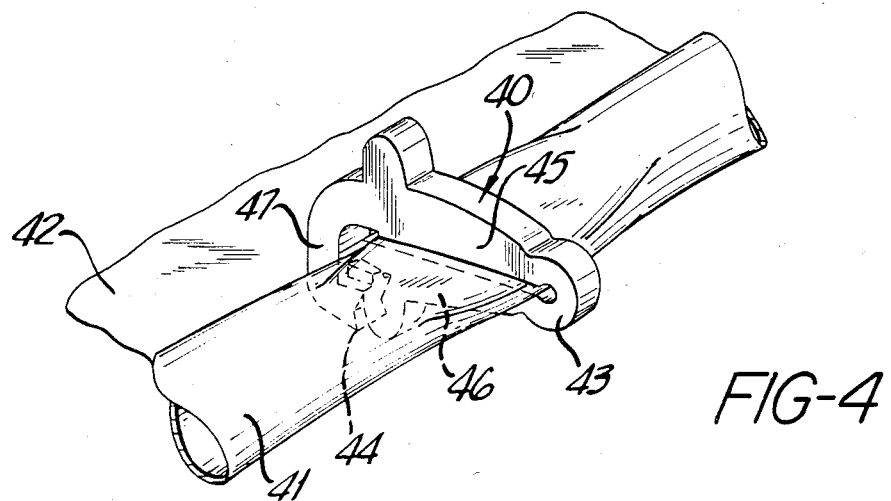
FIG. 4 is a perspective view of the clip depicted in FIG. 1 in a closed position about a blood vessel.
Figure 4A:
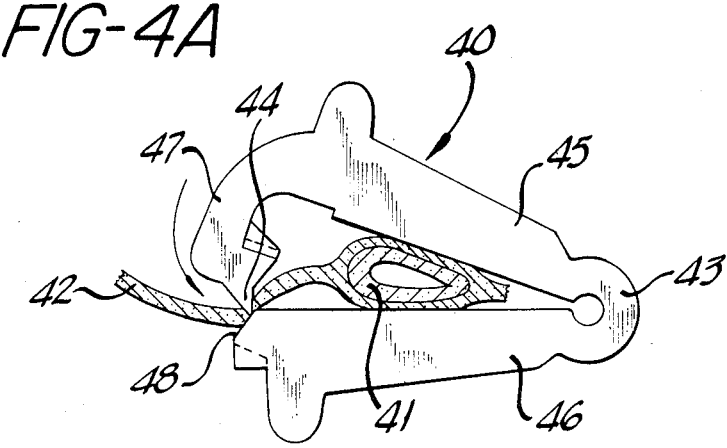
FIG. 4a is a side view of a hemostatic clip of the present invention immediately prior to the clip being closed about a vessel to be ligated.
Figure 4B:
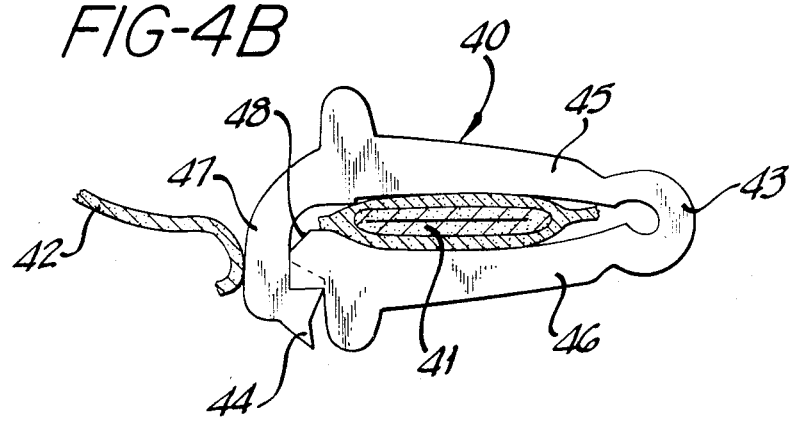
FIG. 4b is a side view of the clip of FIG. 4 with the clip in the fully closed position.

As may be more clearly seen in FIGS. 4, 4a, and 4b when the clip 40 is clamped about a vessel 41 to be closed, assuming that the vessel has not been fully dissected from the surrounding connective tissue 42, (such as would be found in the mesentary) the vessel clamping surfaces are placed on opposite sides of the vessel and the leg members urged together about the resilient hinge 43. The penetrating sharpened end 44 of the one leg member 45 will pinch and scrape the connective tissue between itself and the camming surface 48 of the other leg member 46. This scrapping action enhances the tissue penetrating ability of the sharpened end. Once the tissue is penetrated the usual sequence of closure takes place. As the leg members are urged closer together the leg member 46 continues to deflect the hook portion 47 and becomes engaged by the leg member 45, thereby locking the clip in place about the vessel without tissue interference with latch security. Though in the embodiment shown the penetrating means is a sharpened beveled end, the penetrating means may have other configurations such as a pointed end tapered at a plurality of sides, a pointed end, a plurality of pointed ends, etc.

Figure 5:
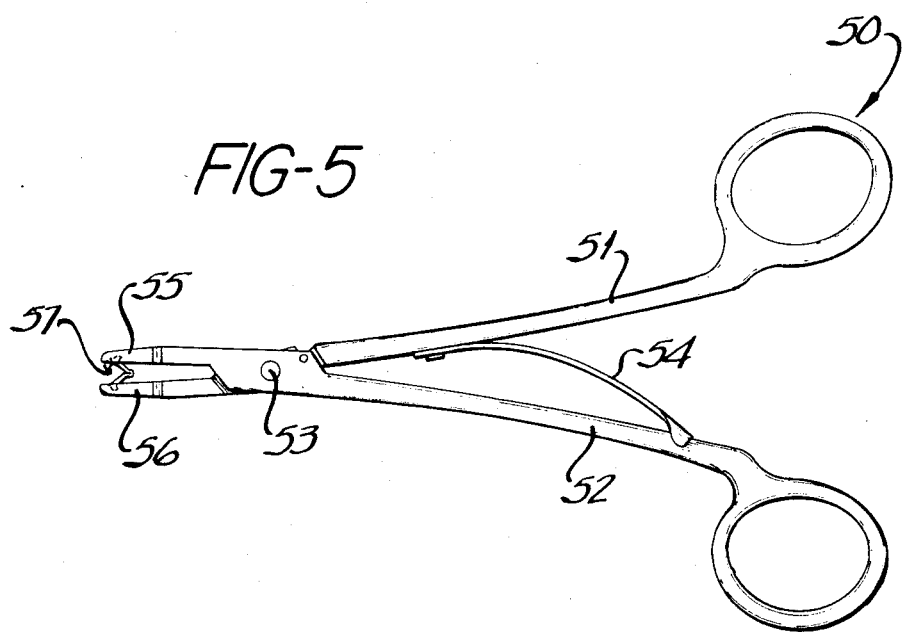
FIG. 5 is a side view of one type of instrument that may be used in applying the clips of the present invention.

In FIG. 5 there is shown a simplified drawing of an instrument for applying the clips of the present invention. This instrument 50 comprises a pair of handles 51 and 52 which are connected together at a hinge point 53. The handles are biased with respect to one another by a spring 54. One of handles extends beyond the hinge point in a first jaw member 55 and the opposite handle extends beyond the hinge point in a complementary second jaw member 56. The instrument engaging means comprises cylindrical bosses extending from the back surfaces of the leg members of the clip 57. These bosses fit into recesses in the jaws of the instrument.

The clip is placed in the jaws with the cylindrical bases in the appropriate recesses. The vessel clamping surfaces of the clip are then placed on opposite sides of the vessel to be closed and the instrument handles urged together closing and locking the clip about the vessel and shutting off the vessel.

Figure 6:
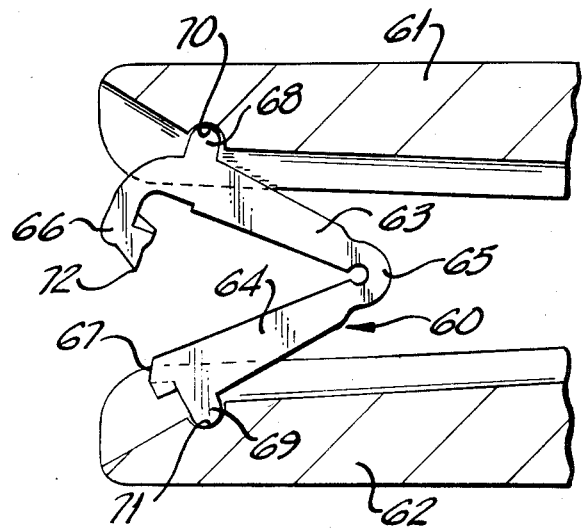
FIG. 6 is an enlarged side view of an improved clip of the present invention in an open position and held in the jaws of the clip applying instrument depicted in FIG. 5.
Figure 7:
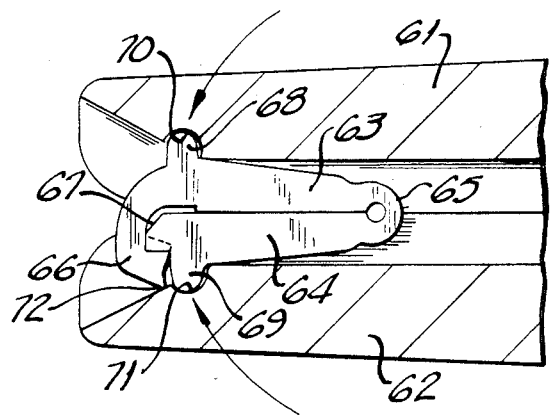
FIG. 7 is an enlarged side view of the clip shown in FIG. 6 in the closed position in the jaws of the instrument depicted in FIG. 5.

FIGS. 6 and 7 show an enlarged view of the jaws and the recesses in the jaws for holding the clip. In FIG. 6 the clip 60 is in the open position in the jaws 61 and 62; whereas, in FIG. 7 the clip 60 has been closed by the jaws of the instrument. The clip comprises a pair of leg members 63 and 64 connected at their proximal ends by a resilient hinge 65. One of the leg members terminates in a return bend portion 66 which is deflectable. The other leg member terminates in an obtuse angle at its end surface 67. On the outer surface of each leg member is a cylindrical boss 68 and 69. The bosses are engaged by complementary recesses 70 and 71 in the jaws of the instrument. As may be seen, the ends of the jaws have been sloped away from the general surfaces of the jaws. The reasons for this are more clearly seen in FIG. 7. As may be seen in FIG. 7, as the leg members are urged towards one another, the deflectable hook portion is deflected and engages the end of the second leg member. The deflectable hook portion includes a penetrating point or blade 72 which is a sharpened point. As the clip is closed, the penetrating point will separate and penetrate through the tissue still attached to the vessel to be closed. The cut-away portions of the jaws of the instrument allow the deflectable portion and the sharpened point free movement about the other leg member so that the clip may be closed as is seen in FIG. 7. In the preferred embodiments of the clip of the present invention as the clip is closed the point or blade scrapes along the end surface 67 of the opposite leg member. This scraping action enhances the penetration of the tissue by the penetrating point or blade.

Figure 8:
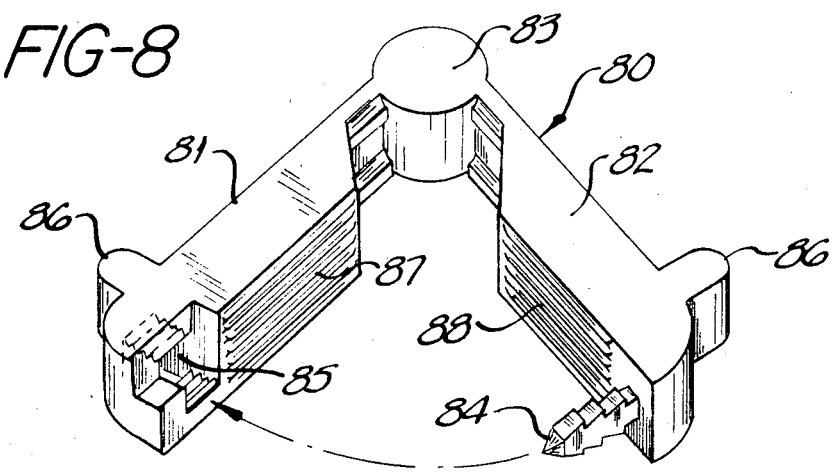
FIG. 8 is a perspective view of another embodiment of the improved hemostatic clip of the present invention.

In FIG. 8 there is shown another embodiment of the improved clip of the present invention. In this embodiment, the clip 80 comprises a pair of leg members 81 and 82 connected at their proximal ends by a double strap type hinge portion 83. At the distal end of one leg member there is a sharp pointed sawed tooth protrusion 84. At the distal end of the opposite leg member there is an interlocking opening 85 for accepting the protrusion. The leg members on each of their outer surfaces carry an appropriate instrument engaging means 86 for applying the clip. In use, the vessel clamping surfaces 87 and 88 are placed on opposite sides of the vessel to be closed. The legs are urged together and the sharpened protrusion readily penetrates any tissue still attached or surrounding the vessel. The legs are urged together and the protrusion engaged by the opening in the distal end of the opposite leg member and the clip locked closing the vessel.

It should be pointed out that although I've shown resilient hinges connecting the leg members, other types of connecting means such as non-resilient hinges or interlocking means may be used to connect the proximal ends of the leg members. Also, as may be appreciated, the distal ends of the leg members may have other interlocking means. What is important is that the distal end of at least one of the leg members includes or carry a penetrating means to allow that distal end to penetrate connective tissue and allow the clip to be closed and locked about the vessel thus providing hemostasis.

The clips of the present invention may be made from various polymeric materials, either absorbable or non-absorbable. Suitable absorbable polymer materials are the polymers and copolymers, of glycolides, lactides, polydioxanones, and the like. Suitable non-absorbable polymeric materials are nylon, polypropylene, polyesters, etc. The clips of the present invention are provided in a sterile state ready for medical and surgical uses. Depending on the polymeric material used, the clips may be sterilized either by heat, radiation, ethylene oxide treatment or other well known sterilization methods.

Having now described the present invention, it will be readily apparent to those skilled in the art that various modifications and variations may be made without departing from the spirit and scope of the present invention.

What is claimed is:

1. A hemostatic clip made from a polymer material, said clip comprising a pair of leg members connected at their proximal ends, said leg members diverging from each other from the proximal ends to the distal ends thereof whereby said leg members may be placed on opposite sides of the vessel to be closed, said clip having an interlocking latch means at the distal ends of said leg members, said latch means comprising a return bend deflectable hook portion disposed at the distal end of the first leg member, said hook portion comprising a first section extending outwardly from and in line with said first leg member, a second section extending downwardly towards the second leg member from the outer most end of said first section and a third section extending rearwardly towards the proximal end of said leg member from the most downwardly extending end of said second section, said third section having two side surfaces top and bottom surfaces, and an end surface, said end surface extending below the general plane of said bottom surface and being tapered back to said bottom surface to form a sharp pointed member, said second leg member terminating at its distal end in a configuration to be engaged by the deflectable hook portion of said first leg member when said clip is closed, whereby when the clip is placed on a vessel to be closed and the leg members urged towards one another, the sharp pointed member of the first leg member scraps against the distal end of said second leg member to penetrate and displace connective tissue adjacent the vessel to be closed and ensure said latch means interlocks when the clip is closed about the vessel.

2. The hemostatic clip according to claim 1 wherein the distal end of said leg member is beveled to act as a camming surface and the sharp pointed member of said first leg member scraps against said beveled surface as the clip is closed.

* * * * *

UNITED STATES PATENT AND TRADEMARK OFFICE
CERTIFICATE OF CORRECTION

PATENT NO. : 4,579,118

DATED : April 1, 1986

INVENTOR(S) : Stephen J. Failla

It is certified that error appears in the above-identified patent and that said Letters Patent is hereby corrected as shown below:

IN THE ABSTRACT THE FIRST SENTENCE WAS LEFT OUT. IT SHOULD READ:--AN IMPROVED HEMOSTATIC CLIP. THE CLIP HAS A PAIR OF LEG MEMBERS WHICH PIVOT ABOUT A HINGE FROM AN OPEN TO A CLOSED POSITION --.

Signed and Sealed this

Twenty-second Day of July 1986

[SEAL]

Attest:

DONALD J. QUIGG

Attesting Officer

Commissioner of Patents and Trademarks